(12) United States Patent
Mochizuki (10) Patent No.: US 10,307,522 B2
(45) Date of Patent: Jun. 4, 2019

(54) BLOOD PURIFICATION APPARATUS

(71) Applicant: Nikkiso Company Limited, Tokyo (JP)

(72) Inventor: Hiroaki Mochizuki, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 233 days.

(21) Appl. No.: 15/343,699

(22) Filed: Nov. 4, 2016

(65) Prior Publication Data

US 2017/0072122 A1    Mar. 16, 2017

Related U.S. Application Data

(63) Continuation of application No. PCT/JP2015/063659, filed on May 12, 2015.

(30) Foreign Application Priority Data

May 12, 2014    (JP) .................................. 2014-098612

(51) Int. Cl.
  *A61M 1/14* (2006.01)
  *A61M 1/16* (2006.01)
  (Continued)

(52) U.S. Cl.
  CPC ............ *A61M 1/1603* (2014.02); *A61M 1/14* (2013.01); *A61M 1/1605* (2014.02);
  (Continued)

(58) Field of Classification Search
  None
  See application file for complete search history.

(56) References Cited

U.S. PATENT DOCUMENTS 5,441,636 A    8/1995    Chevallet et al.
6,685,831 B2    2/2004    Dönig et al.
(Continued)

FOREIGN PATENT DOCUMENTS

CN    101304773 A    11/2008
EP    2005982 A1    12/2008
(Continued)

OTHER PUBLICATIONS

Extended European Search Report, Application No. 15793590.9 dated Nov. 20, 2017.
(Continued)

*Primary Examiner* — Chester T Barry
(74) *Attorney, Agent, or Firm* — The Dobrusin Law Firm, PC (57) ABSTRACT

A blood purification apparatus is provided that allows setting work at the time of blood purification treatment or preparation for the treatment to be easily and smoothly performed. The blood purification apparatus includes: a circuit for blood purification having an arterial blood circuit and a venous blood circuit that constitute a blood circuit; a dialyzer for purifying the blood extracorporeally circulated by the blood circuit; and a dialysis device main body, wherein the blood purification apparatus includes an identification means that allows specific information to be identified, the specific information including an operating condition of the circuit for blood purification or the dialyzer at the time of blood purification treatment or preparation for the treatment, a reading means by which the specific information of the identification means is readable, and a control unit that performs blood purification treatment or preparation for the treatment based on the operating condition in the specific information read by the reading means.

12 Claims, 10 Drawing Sheets

(51) Int. Cl.
  *A61M 1/26* (2006.01)
  *A61M 1/34* (2006.01)
  *A61M 1/36* (2006.01)
  *A61M 39/10* (2006.01)

(52) U.S. Cl.
  CPC .......... *A61M 1/267* (2014.02); *A61M 1/3424* (2014.02); *A61M 1/367* (2013.01); *A61M 39/10* (2013.01); *A61M 1/3644* (2014.02); *A61M 2205/14* (2013.01); *A61M 2205/18* (2013.01); *A61M 2205/276* (2013.01); *A61M 2205/3569* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/60* (2013.01); *A61M 2205/6018* (2013.01); *A61M 2205/6072* (2013.01)

(56) References Cited

U.S. PATENT DOCUMENTS

| | | | |
|---|---|---|---|
| 7,488,301 | B2 | 2/2009 | Beden et al. |
| 8,991,414 | B2 | 3/2015 | Gronau et al. |
| 2002/0147423 | A1* | 10/2002 | Burbank ............... A61M 1/282 604/6.16 |
| 2004/0204634 | A1 | 10/2004 | Womble et al. |
| 2006/0079826 | A1 | 4/2006 | Beden et al. |
| 2009/0101566 | A1 | 4/2009 | Crnkovich et al. |
| 2010/0274168 | A1 | 10/2010 | Gronau et al. |
| 2010/0274172 | A1 | 10/2010 | Guenther et al. |
| 2012/0000547 | A1 | 1/2012 | Gronau et al. |
| 2012/0123322 | A1 | 5/2012 | Scarpaci et al. |
| 2012/0181331 | A1* | 7/2012 | Beden ................. A61M 1/3621 235/375 |
| 2013/0228505 | A1* | 9/2013 | Burbank ............. A61M 1/1656 210/257.2 |
| 2015/0021244 | A1 | 1/2015 | Furuhashi et al. |
| 2016/0175508 | A1 | 6/2016 | Murakami et al. |

FOREIGN PATENT DOCUMENTS

| | | |
|---|---|---|
| EP | 2292284 A1 | 3/2011 |
| JP | S60-153138 U1 | 10/1985 |
| JP | S62-070529 U1 | 5/1987 |
| JP | S63-106445 U1 | 7/1988 |
| JP | H06-292722 A | 10/1994 |
| JP | 2002-095741 A | 4/2002 |
| JP | 2004-016619 A | 1/2004 |
| JP | 2006-280775 A | 10/2006 |
| JP | 2006-314458 A | 11/2006 |
| JP | 2007-007435 A | 1/2007 |
| JP | 2007-167108 A | 7/2007 |
| JP | 2009-112651 A | 5/2009 |
| JP | 2009-131412 A | 6/2009 |
| JP | 2010-273784 A | 12/2009 |
| JP | 2010-269050 A | 12/2010 |
| JP | 2010-538803 A | 12/2010 |
| JP | 2011-120821 A | 6/2011 |
| JP | 2011-120822 A | 6/2011 |
| JP | 2011-120823 A | 6/2011 |
| JP | 2012-200275 A | 10/2012 |
| JP | 2012-524563 A | 10/2012 |
| JP | 2013-533793 A | 8/2013 |
| JP | 2014-070335 A | 4/2014 |
| WO | 1999/062574 A1 | 12/1999 |
| WO | 2009/081196 A1 | 7/2009 |
| WO | 2011/132123 A1 | 10/2011 |

OTHER PUBLICATIONS

International Search Report from the Japanese Patent Office for Application No. PCT/JP2015/063659, dated Aug. 4, 2015.
Written Opinion from the Japanese Patent Office for Application No. PCT/JP2015/063659, dated Aug. 4, 2015.
Co-pending U.S. Appl. No. 14/497,369, filed Sep. 26, 2014.
Co-pending U.S. Appl. No. 15/055,219, filed Feb. 26, 2016.
Second Chinese Office Action from the State Intellectual Property Office of the People's Republic of China for Application No. 201580024695.X, dated Feb. 19, 2019.

* cited by examiner

| Medical material | Feasible treatment mode | Maximum treatment time | Upper limit of weight of suitable patient | Lower limit of weight of suitable patient | ... |
|---|---|---|---|---|---|
| Blood purifier | | | | | |
| Circuit for blood purification | | | | | |

BLOOD PURIFICATION APPARATUS

FIELD

The present invention relates to a blood purification apparatus for extracorporeally circulating the blood of a patient to purify the blood.

BACKGROUND

In general, a blood purification apparatus for performing hemodialysis treatment includes an arterial blood circuit and a venous blood circuit that constitute a blood circuit for extracorporeally circulating the blood of a patient, a blood purifier for purifying the blood extracorporeally circulated by the blood circuit, and a device main body provided with various treatment means such as a blood pump for performing blood purification treatment by the blood circuit and the blood purifier. An arterial puncture needle and a venous puncture needle are attachable to the leading ends of the arterial blood circuit and the venous blood circuit respectively.

After the arterial puncture needle and the venous puncture needle are inserted in a patient, a blood pump is driven, thereby causing blood of a patient to flow in the arterial blood circuit and the venous blood circuit, and in the process of the flowing, blood purification is performed by the blood purifier. Also, in hemodialysis treatment, a dialysate inlet tube for introducing dialysate into the blood purifier, and a dialysate outlet tube for discharging dialysate from the blood purifier are each connected to the blood purifier.

When blood purification treatment is performed, a blood circuit, a dialysate inlet tube, a dialysate outlet tube, and others (these are referred to as a "circuit for blood purification") are connected to a blood purifier, then the blood purifier is mounted on a device main body, and a treatment mode (such as hemodialysis or hemofiltration), treatment conditions (such as a blood flow rate), various alert ranges according to the mounted circuit for blood purification and the blood purifier are inputted and thereby set by a medical professional. Such prior art is not related to the invention in publicly known literature, thus information on prior art literature to be listed is not provided.

SUMMARY

However, in the above-mentioned conventional blood purification apparatus, a medical professional views labels or the like attached to the circuit for blood purification and the blood purifier mounted on the device main body, and confirms the specification, then later needs to make setting according to the specification. Thus, there is a problem in that work at the time of setting becomes complicated. Such setting is needed not only at the time of blood purification treatment, but also at the time of preparation for the treatment, such as priming, and thus there is a similar problem.

The present invention has been made in view of such a situation, and aims to provide a blood purification apparatus that allows setting work at the time of blood purification treatment or preparation for the treatment to be easily and smoothly performed.

The present teachings comprise: a circuit for blood purification having an arterial blood circuit and a venous blood circuit that constitute a blood circuit for extracorporeally circulating at least blood of a patient; a blood purifier for purifying the blood extracorporeally circulated by the blood circuit; a device main body provided with various treatment means for performing blood purification treatment in the blood circuit and the blood purifier, wherein the blood purification apparatus includes an identification means that allows specific information to be identified, the specific information including an operating condition of the circuit for blood purification or the blood purifier at the time of blood purification treatment or preparation for the treatment, a reading means by which the specific information of the identification means is readable, and a control unit that performs blood purification treatment or preparation for the treatment based on the operating condition in the specific information read by the reading means.

The present teachings provide the blood purification apparatus according to the teachings herein, in which the device main body includes a storage unit that stores the specific information which is read by the reading means, and device main body causes the control unit to perform blood purification treatment or preparation for the treatment based on the operating condition in the specific information stored in the storage unit.

The present teachings provide the blood purification apparatus according to the teachings herein, in which the operating condition as the specific information in the identification means includes a parameter indicating a restriction or an acceptable range related to blood purification treatment or preparation for the treatment.

The present teachings provide the blood purification apparatus according to the teachings herein, in which in addition to the operating condition, the specific information of the identification means includes additional information such as an expiration date of the circuit for blood purification or the blood purifier.

The present teachings provide the blood purification apparatus according to the teachings herein, in which the control unit of the device main body allows a treatment condition to be restricted based on information identified by the identification means.

The present teachings provide the blood purification apparatus according to the teachings herein, in which the blood purifier has a plurality of connecting portions connectable to the circuit for blood purification, respective connection flow paths are extended from the connecting portions of the blood purifier, and the blood purifier and the circuit for blood purification are configured to be connectable via the connection flow paths, the blood purification apparatus comprises a first connector formed by bundling leading ends of the circuit for blood purification, and a second connector formed by bundling leading ends of the connection flow paths, and connection of the first connector and the second connector allows the circuit for blood purification corresponding to the connecting portions of the blood purifier to communicate with each other, and the identification means is formed in the first connector or the second connector.

The present teachings provide the blood purification apparatus according to the teachings herein, in which the device main body includes a holding means that allows the first connector and the second connector to be held only in a state where the first connector and the second connector are connected, and the identification means allows to be identified in a state where the first connector and the second connector are held.

According to the present teachings, the blood purification apparatus includes an identification means that allows specific information to be identified, the specific information including an operating condition of the circuit for blood purification or the blood purifier at the time of blood purification treatment or preparation for the treatment, a reading means by which the specific information of the identification means is readable, and a control unit that performs blood purification treatment or preparation for the treatment based on the operating condition in the specific information read by the reading means. Thus, setting work at the time of blood purification treatment or preparation for the treatment can be easily and smoothly performed.

According to the present teachings, the device main body includes a storage unit that stores the specific information which is read by the reading means, and device main body causes the control unit to perform blood purification treatment or preparation for the treatment based on the operating condition in the specific information stored in the storage unit. Thus, blood purification treatment or preparation for the treatment can be performed more reliably.

According to the present teachings, the operating condition as the specific information in the identification means includes a parameter indicating a restriction or an acceptable range related to blood purification treatment or preparation for the treatment. Thus, a parameter indicating the restriction or acceptable range for the circuit for blood purification and the blood purifier does not need to be pre-stored in the device main body.

According to the present teachings, in addition to the operating condition, the specific information of the identification means includes additional information such as an expiration date of the circuit for blood purification or the blood purifier. Thus, blood purification treatment or preparation for the treatment can be performed by the control unit based on the additional information.

According to the present teachings, the control unit of the device main body allows a treatment condition to be restricted based on information identified by the identification means. Thus, the safety of blood purification treatment can be further improved.

According to the present teachings, the blood purifier has a plurality of connecting portions connectable to the circuit for blood purification, respective connection flow paths are extended from the connecting portions of the blood purifier, and the blood purifier and the circuit for blood purification are configured to be connectable via the connection flow paths, the blood purification apparatus comprises a first connector formed by bundling leading ends of the circuit for blood purification, and a second connector formed by bundling leading ends of the connection flow paths, and connection of the first connector and the second connector allows the circuit for blood purification corresponding to the connecting portions of the blood purifier to communicate with each other, and the identification means is formed in the first connector or the second connector. Thus, work of connection between the circuit for blood purification and the blood purifier can be easily performed, and setting work at the time of blood purification treatment or preparation for the treatment can be easily and smoothly performed.

According to the present teachings, the device main body includes a holding means that allows the first connector and the second connector to be held only in a state where the first connector and the second connector are connected, and the identification means allows to be identified in a state where the first connector and the second connector are held. Thus, at the time of identification of the identification means, it is always the case that the first connector and the second connector are in a connected state, and failure of connection between the first connector and the second connector can be reliably prevented.

DETAILED DESCRIPTION

Hereinafter, an embodiment of the present invention will be specifically described with reference to the drawings. A blood purification apparatus according to the present embodiment is applied to a dialysis apparatus for extracorporeally circulating the blood of a patient to purify the blood, and mainly includes circuit 1 for blood purification, a dialyzer 2 as a blood purifier, a first connector 3, a second connector 4, and a dialysis device main body 8 (corresponding to the "device main body" of the present invention) having a reading means 13 and a control unit 17 as illustrated in FIGS. 1 to 11.

The dialyzer 2 is formed by housing in a case unit a plurality of hollow fibers in which fine holes (bores) are formed, and in the case unit, a blood inlet port 2a, a blood outlet port 2b, a dialysate inlet port 2c, and a dialysate outlet port 2d are formed as a plurality of connecting portions connectable to the circuit 1 for blood purification. Also, in the present embodiment, respective connection flow paths (a to d) formed of a flexible tube are extended from the blood inlet port 2a, the blood outlet port 2b, the dialysate inlet port 2c, and the dialysate outlet port 2d.

The circuit 1 for blood purification has an arterial blood circuit 1a having an base end to which an arterial puncture needle is attachable, a venous blood circuit 1b having an base end to which a venous puncture needle is attachable, dialysate inlet tubes (1c, 1d, 1e, 1f) that introduce dialysate into the dialyzer 2, and dialysate outlet tubes (1g, 1h) that discharge dialysate (drainage) from the dialyzer 2. Also, the circuit 1 for blood purification according to the present embodiment has substitution fluid inlet tubes (1e', 1f') which are branched off from the dialysate inlet tube 1e. In addition, the circuit 1 for blood purification according to the present embodiment has a main body H, and flexible tubes (D1 to D5) to be peristaltic are formed in the main body H.

The flexible tube D1 to be peristaltic is connected to some midpoint (between tubes 1aa and 1ab included in the arterial blood circuit) in the arterial blood circuit 1a, and is attached to peristaltic pump P1 (blood pump) provided in the dialysis device main body 8. Also, the flexible tube D2 to be peristaltic is connected to some midpoint of the dialysate inlet tubes (1c, 1d), the flexible tube D3 to be peristaltic is connected to some midpoint of the substitution fluid inlet tubes (1e', 1f'), and both tubes are attached to the peristaltic pumps P2, P3, respectively provided in the dialysis device main body 8. Furthermore, the flexible tube D4 to be peristaltic is connected to some midpoint of the dialysate outlet tubes (1g, 1h) and is attached to the peristaltic pump P4 provided in the dialysis device main body 8. It is to be noted that the flexible tube D5 to be peristaltic is attached to the peristaltic pump P5, and liquid accumulated in a storage bag B2 is discharged out of the system by driving, and thereby the accuracy of a weight scale 7 can be ensured.

The main body H is then fitted and mounted in a portion (stator) of the dialysis device main body 8, where the peristaltic pumps P1 to P5 are provided (see FIGS. 1, 2), a cover 12 is closed (see FIG. 3), and the flexible tubes (D1 to D4) to be peristaltic are thereby collectively mounted on the peristaltic pumps (P1 to P4). Thus, when the arterial puncture needle and the venous puncture needle are inserted in a patient, then the peristaltic pump P1 (blood pump) is driven, the blood of the patient can be extracorporeally circulated in the arterial blood circuit 1a and the venous blood circuit 1b.

Also, the base end (base end of the tube 1c) of the dialysate inlet tubes (1c, 1d, 1e, 1f) is connected to a storage bag B1 that stores dialysate to be supplied to the dialyzer 2, a warming bag 5 for warming the dialysate is connected to some point (between the tube 1d and the tube 1e), and the base end (base end of the tube 1h) of the dialysate outlet tubes (1g, 1h) is connected to a storage bag B2 that stores the dialysate (drainage) discharged from the dialyzer 2.

When the peristaltic pump P2 is driven, the dialysate in the storage bag B1 flows to the dialyzer 2 and when the peristaltic pump P4 is driven, the dialysate (drainage) in the dialyzer 2 flows to the storage bag B2. It is to be noted that the storage bags B1, B2 are configured to be hooked into respective hooks F provided in the dialysis device main body 8, and the weights of the storage bags are measured by weight scales 6, 7 in real time. Consequently, it is possible to supply dialysate to the dialyzer 2 at a set flow rate and to discharge the dialysate from the dialyzer 2.

Also, in the present embodiment, the flexible tube D3 to be peristaltic is connected between the substitution fluid inlet tube 1e' branched off from the dialysate inlet tube 1e and the substitution fluid inlet tube 1f' connected to the venous blood circuit 1b, and the flexible tube D3 to be peristaltic is mounted on the peristaltic pump P3. Driving the peristaltic pumps P2, P3 allows the dialysate in the storage bag B1 to be supplied to the venous blood circuit 1b for substitution. It is to be noted that the leading end of the substitution fluid inlet tube 1f may be connected to the arterial blood circuit 1a to supply the dialysate to the arterial blood circuit 1a for substitution.

Figure 1:
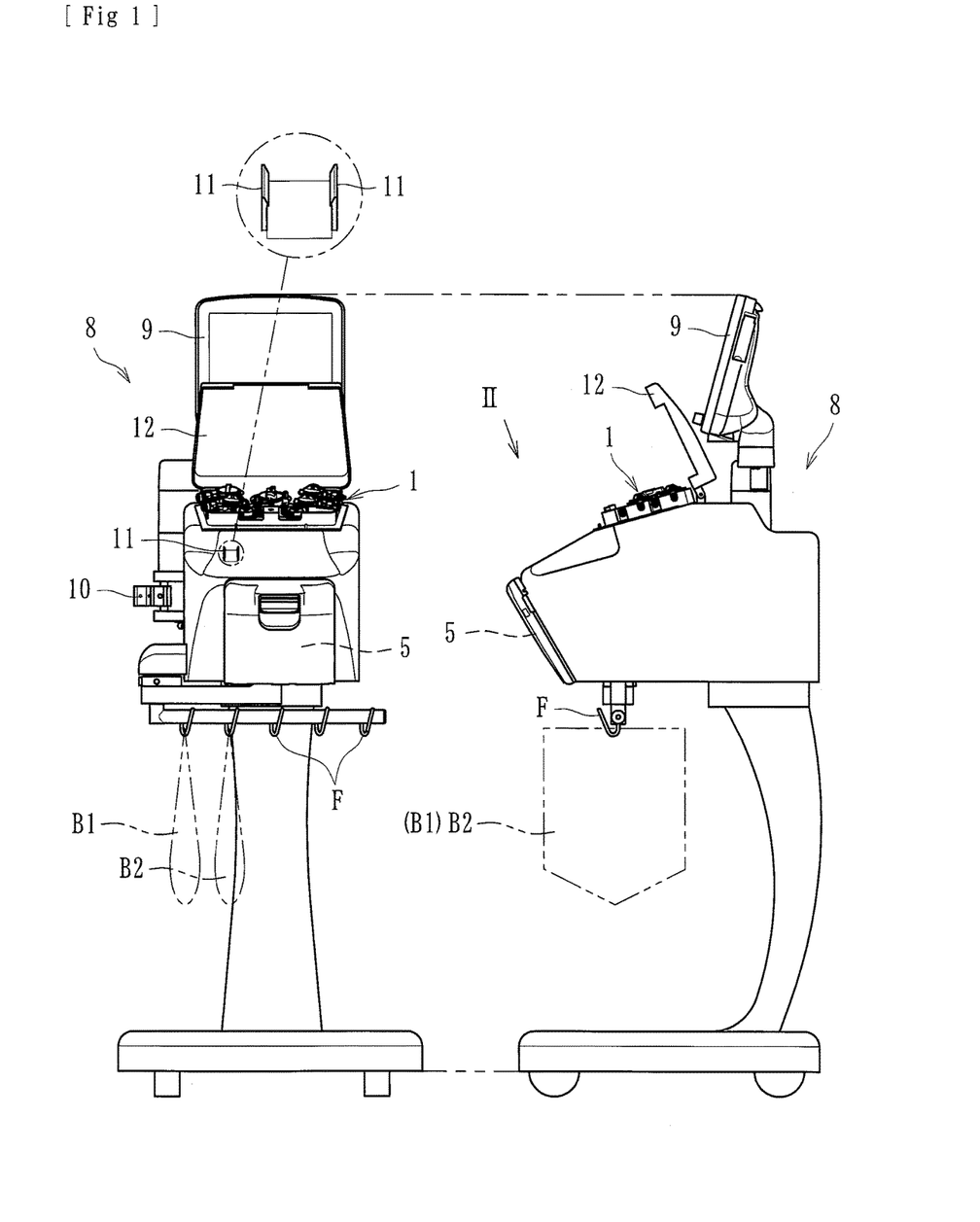
FIG. 1 provides a front view and a side view illustrating a blood purification apparatus (a state before the blood purifier and the connectors are mounted on the device main body) according to an embodiment of the present invention.
Figure 2:
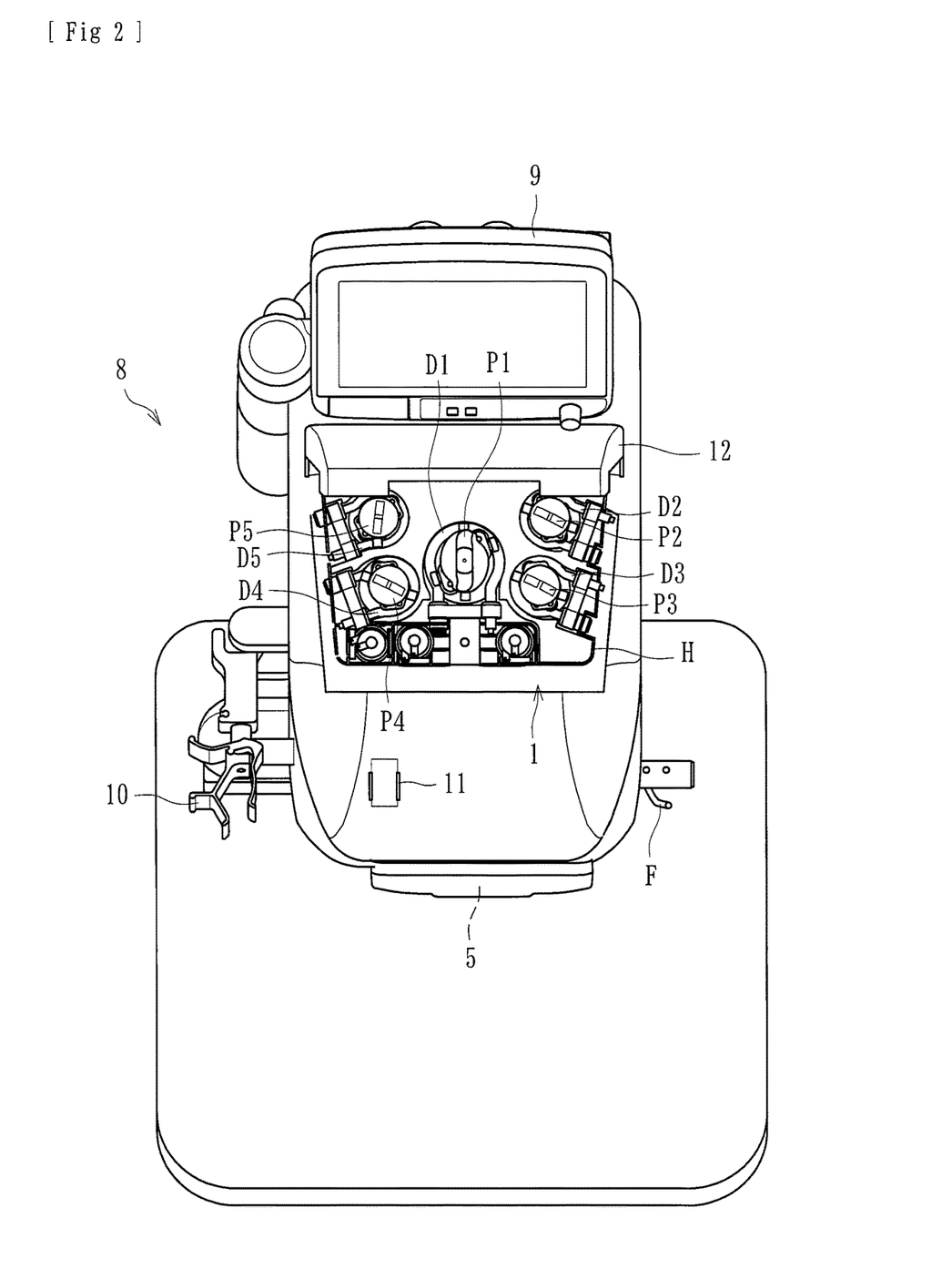
FIG. 2 is a view as seen from an arrow II in FIG. 1.
Figure 3:
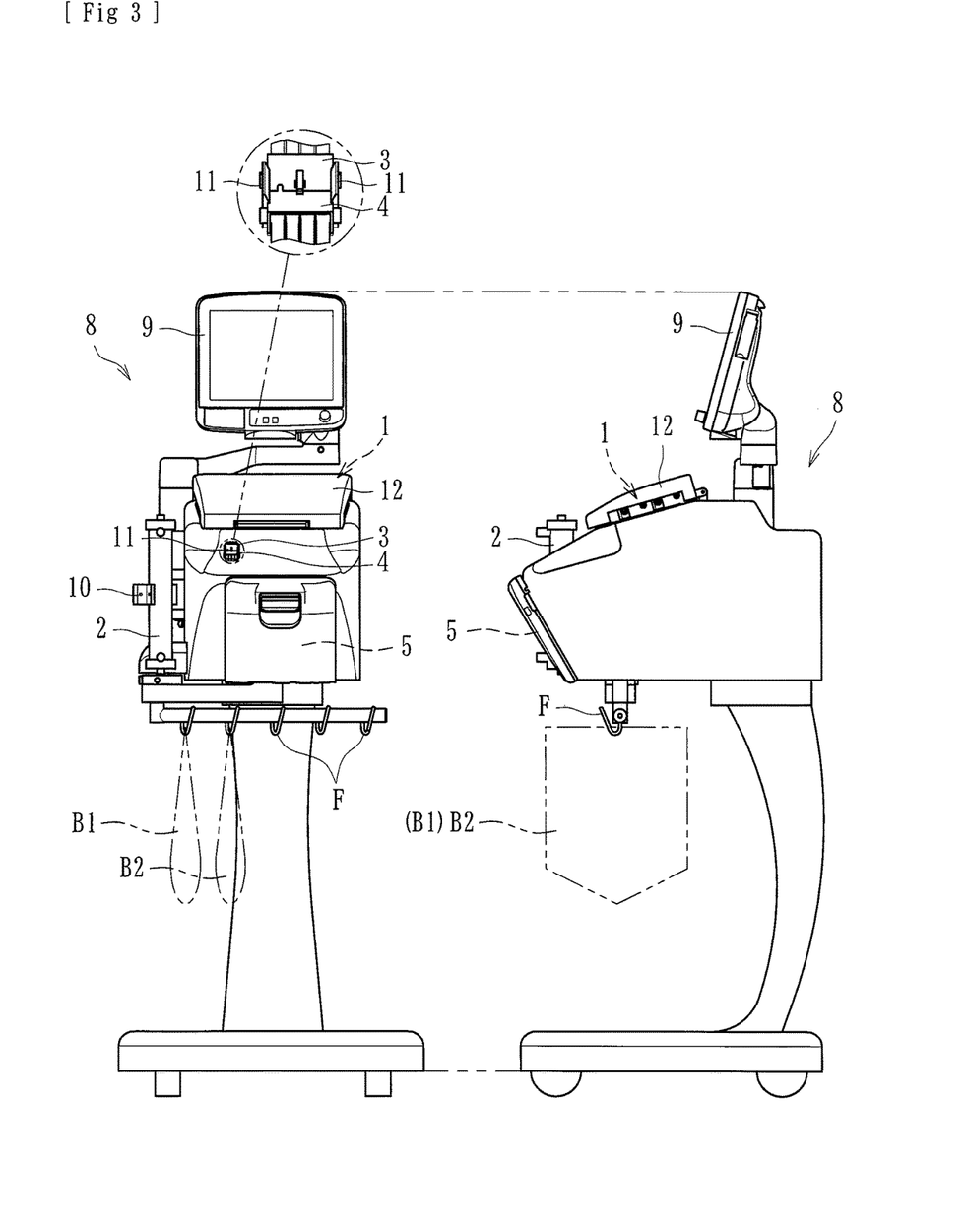
FIG. 3 provides a front view and a side view illustrating the blood purification apparatus (a state where the blood purifier and the connectors are mounted on the device main body).
Figure 4:
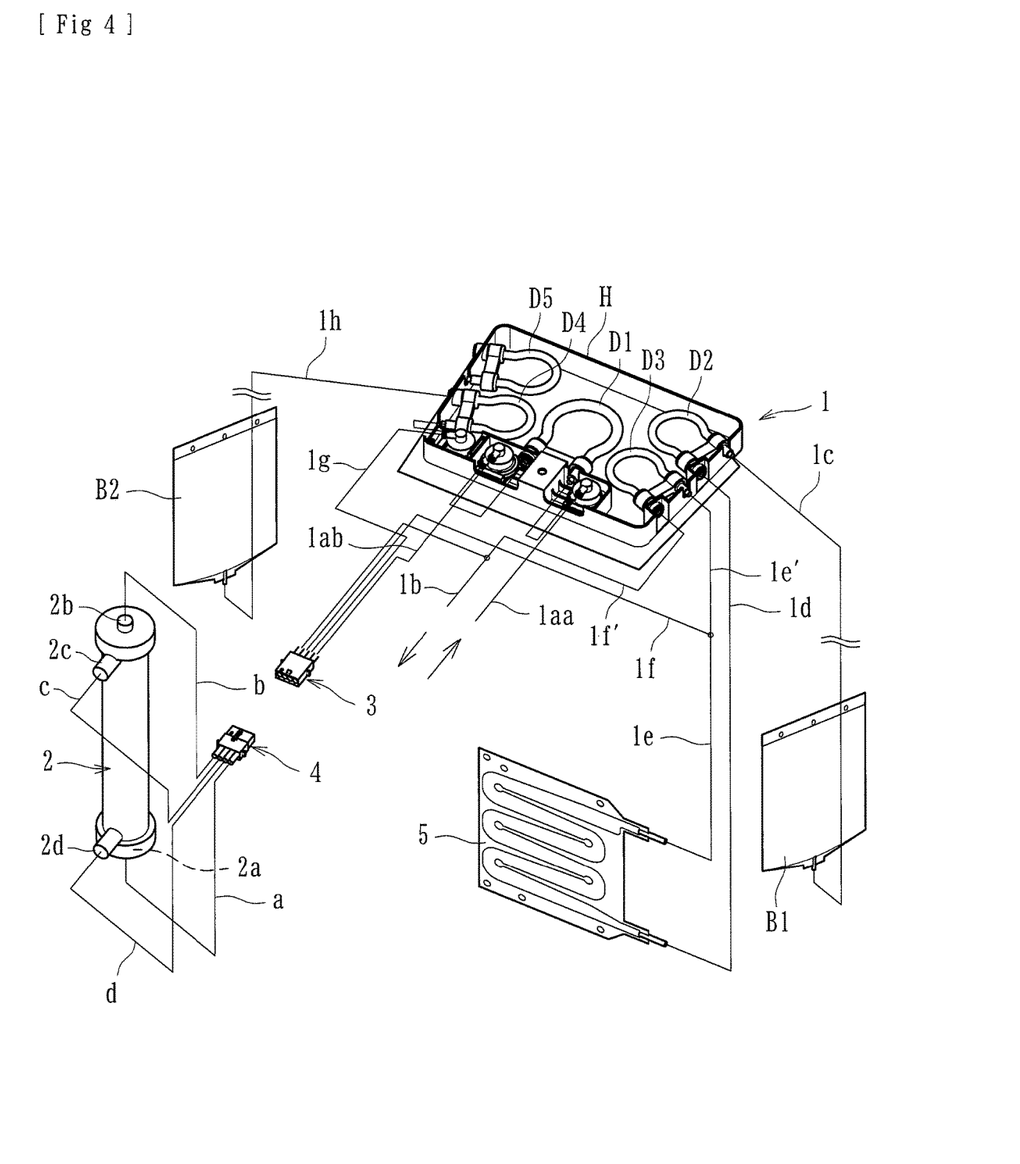
FIG. 4 is a schematic view illustrating a connection relationship between the first connector and the second connector in the blood purification apparatus.
Figure 5:
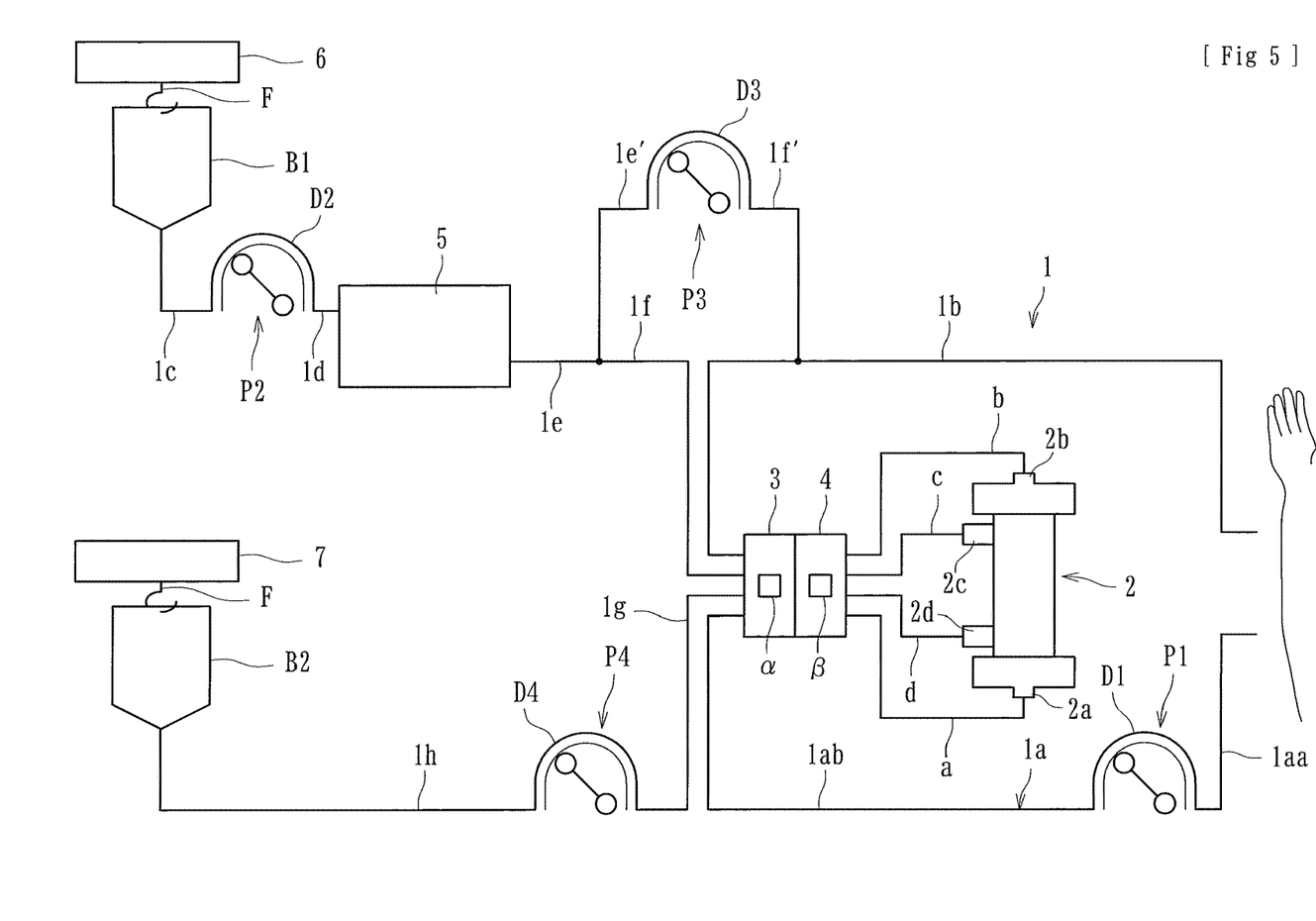
FIG. 5 is a schematic diagram illustrating a connection relationship at the time of blood purification treatment in the blood purification apparatus.
Figure 6:
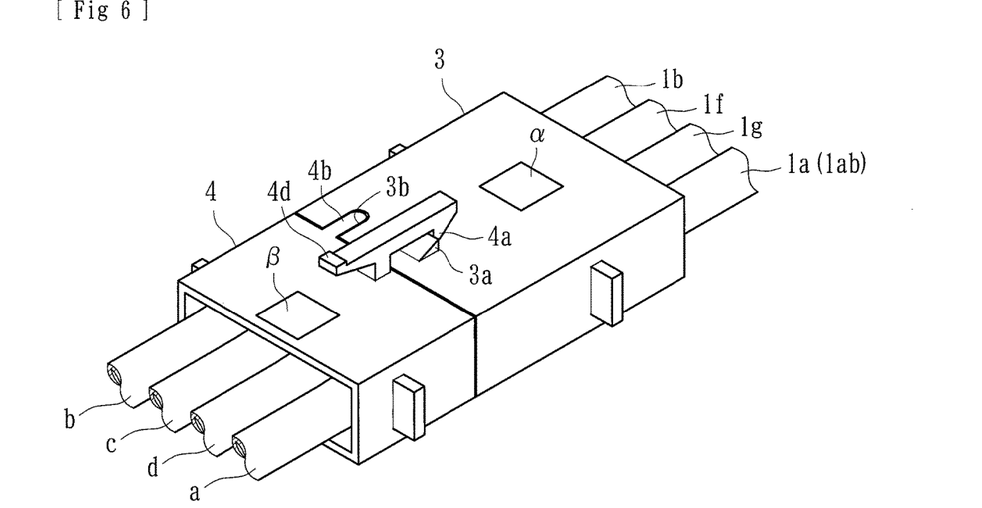
FIG. 6 is a perspective view illustrating a state where the first connector and the second connector are connected in the blood purification apparatus.
Figure 7:
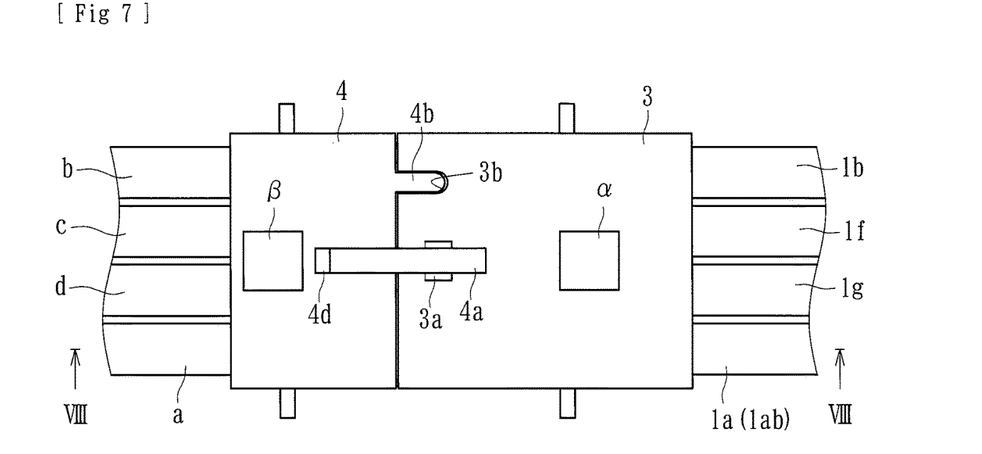
FIG. 7 is a plan view illustrating a state where the first connector and the second connector are connected in the blood purification apparatus.

Here, in the present embodiment, respective connection flow paths (a to d) are extended from the connecting portions (ports) of the dialyzer 2 (blood purifier), the dialyzer 2 and the circuit 1 for blood purification are configured to be connectable via the connection flow paths (a to d), and the blood purification apparatus includes the first connector 3 formed by bundling the leading ends (specifically, the leading ends of tube lab of the arterial blood circuit 1a, the venous blood circuit 1b, tube 1f of the dialysate inlet tube, tube 1g of the dialysate outlet tube) of the circuit 1 for blood purification, and the second connector 4 formed by bundling the leading ends of the connection flow paths (a to d) extended from the ports of the dialyzer 2. As illustrated in FIGS. 6, 7, the first connector 3 and the second connector 4 are connected, thereby allowing the circuit for blood purification corresponding to the connecting portions (the ports) of the dialyzer 2 (blood purifier) to communicate with each other.

Figure 9:
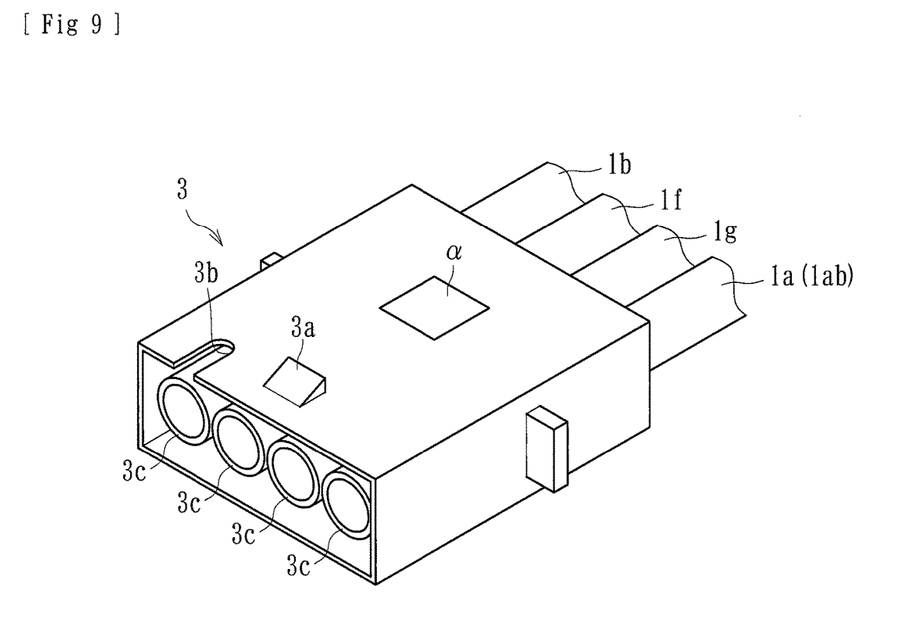
FIG. 9 is a perspective view illustrating the first connector in the blood purification apparatus.
Figure 10:
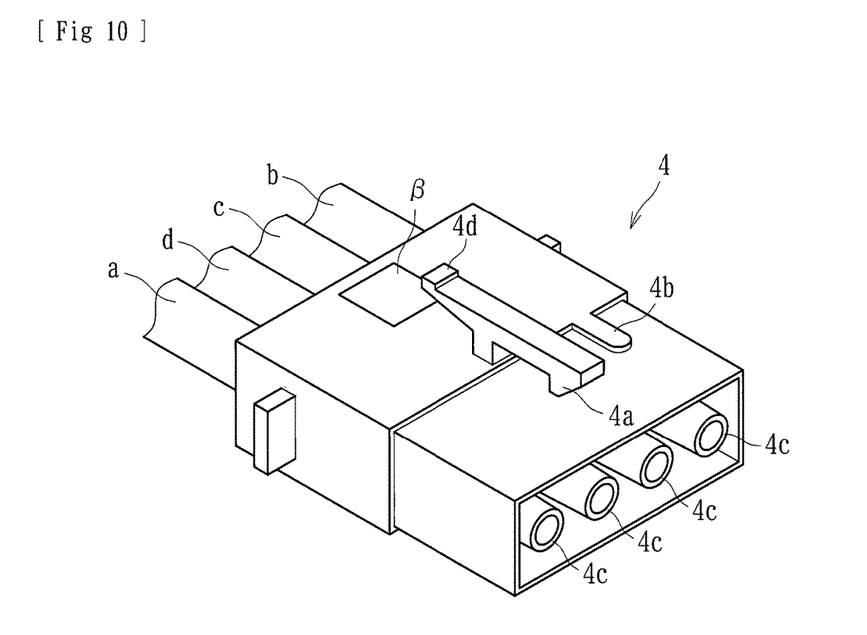
FIG. 10 is a perspective view illustrating the second connector in the blood purification apparatus.

As illustrated in FIG. 9, in the first connector 3, a retained portion 3a, a depressed shape 3b, and connection ports 3c communicating with the leading ends of the circuit 1 for blood purification are formed, and as illustrated in FIG. 10, in the second connector 4, a retaining pawl 4a, a projecting shape 4b, and connection ports 4c communicating with the leading ends of the connection flow paths (a to d) are formed. When the first connector 3 and the second connector 4 are connected, as illustrated in FIGS. 6, 7, the retaining pawl 4a is retained in the retained portion 3a and the projecting shape 4b is fitted in the depressed shape 3b.

Thus, in a state where the first connector 3 and the second connector 4 are connected, the retaining pawl 4a is retained in the retained portion 3a, and thus it is possible to prevent accidental release of the connection between the first connector 3 and the second connector 4. It is to be noted that an operation section 4d for releasing retention of the retaining pawl 4a is formed in the second connector 4, and connection between the first connector 3 and the second connector 4 can be released by operating the operation section 4d.

Also, in a state where the first connector 3 and the second connector 4 are connected, the projecting shape 4b is configured to be fitted in the depressed shape 3b, and thus connection is possible only with proper type or direction of connection. In other words, when the type of the first connector 3 and the second connector 4 is not proper or when directions are reverse to each other, the projecting shape 4b is designed not to be fitted in the depressed shape 3b, and it is possible to prevent accidental connection between the first connector 3 and the second connector 4. In the present embodiment, in part of the first connector 3 and the second connector 4, the shapes (the depressed shape 3b and the projecting shape 4b) are formed that allow connection only with proper type or direction of connection. However, the entire connecting portion between the first connector 3 and the second connector 4 may be a shape that allows connection only with proper type or direction of connection.

Figure 8:
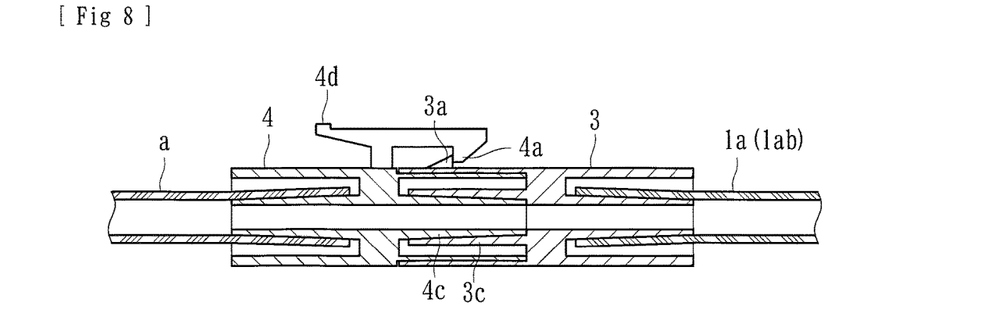
FIG. 8 is a sectional view taken along line VIII-VIII in FIG. 7.

Furthermore, in a state where the first connector 3 and the second connector 4 are connected, connection ports 3c is configured to be firmly fitted in respective connection ports 4c as illustrated in FIG. 8. Thus, the circuit 1 for blood purification and the connection flow paths (a to d) communicate with each other to allow flow of liquid, and the leading end of the circuit 1 for blood purification and the leading ends of the connection flow paths (a to d) are sealed, and leakage at the time of liquid flow is prevented. It is to be noted that in a state where the first connector 3 and the second connector 4 are connected, a separate seal material may be provided that seals the leading end of the circuit 1 for blood purification and the leading ends of the connection flow paths (a to d).

Figure 14:
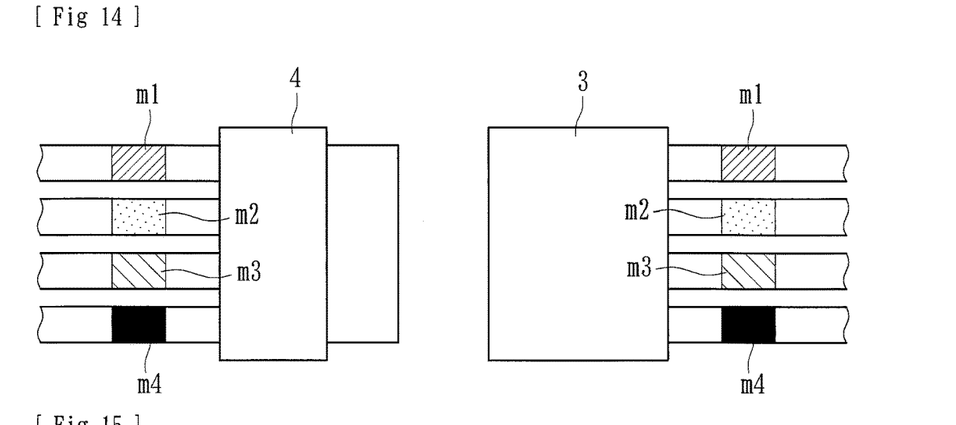
FIG. 14 is a schematic view illustrating a first connector and a second connector in a blood purification apparatus according to another embodiment of the present invention.
Figure 15:
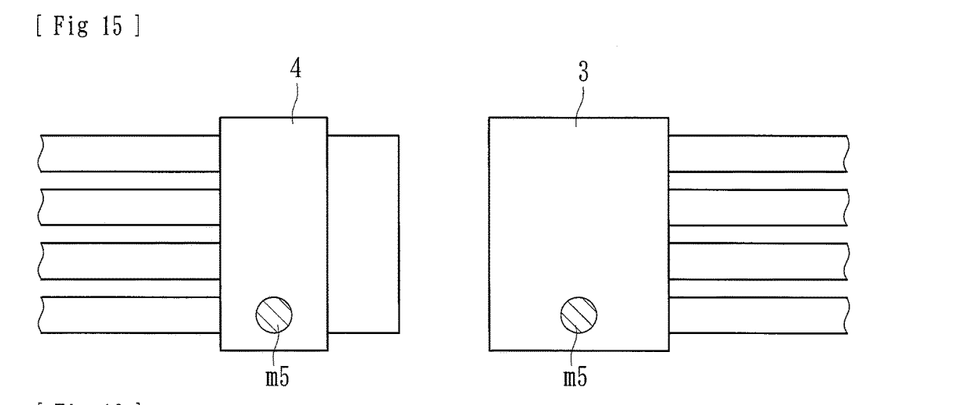
FIG. 15 is a schematic view illustrating a first connector and a second connector in a blood purification apparatus according to another embodiment of the present invention.
Figure 16:
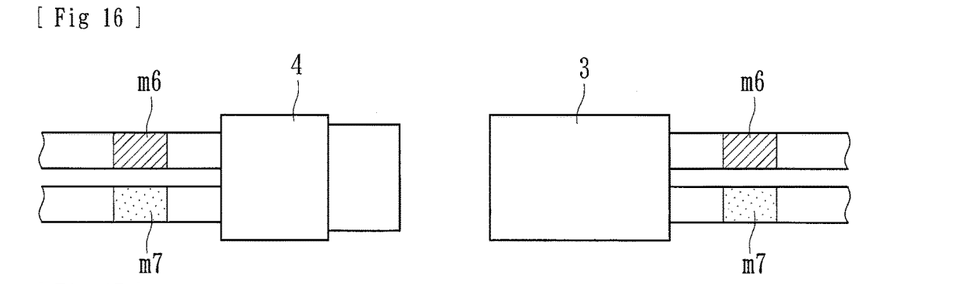
FIG. 16 is a schematic view illustrating a first connector and a second connector in a blood purification apparatus according to another embodiment of the present invention.
Figure 17:
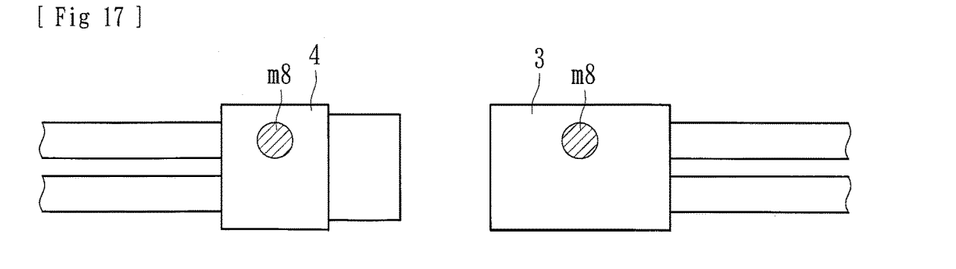
FIG. 17 is a schematic view illustrating a first connector and a second connector in a blood purification apparatus according to another embodiment of the present invention.

Thus, a mark, which allows visual identification of proper type or direction of connection, may be formed in the first connector 3 and the second connector 4. For instance, as illustrated in FIG. 14, colored portions m1 to m4 (marks) in any different colors may be formed in respective tubes connected to the first connector 3, and colored portions m1 to m4 being colored corresponding to the respective tubes connected to the second connector 4 may be formed. As illustrated in FIG. 15, mark m5 may be formed in each of the first connector 3 and the second connector 4 to allow visual identification of proper type or direction of connection. It is to be noted that the number of tubes connected to the first connector 3 and the second connector 4 is not limited to four, and may be any number (multiple number), and even in this case, it is preferable to form marks m6, m7 in different colors or mark m8 as illustrated in FIGS. 16, 17.

Thus, connection between the first connector 3 and the second connector 4 causes the arterial blood circuit 1a to be connected to the blood inlet port 2a via the connection flow path a, the venous blood circuit 1b to be connected to the blood outlet port 2b via the connection flow path b, the dialysate inlet tubes (1c, 1d, 1e, 1f) to be connected to the dialysate inlet port 2c via the connection flow path c, and the dialysate outlet tubes (1g, 1h) to be connected to the dialysate outlet port 2d via the connection flow path d. Thus, in the process of extracorporeally circulating the blood of a patient, it is possible to purify the blood by the dialyzer 2 and to supply and discharge the dialysate to and from the dialyzer 2.

Furthermore, in the first connector 3 and the second connector 4 according to the present embodiment, identification means α, β are formed, which allow specific information on the circuit 1 for blood purification or the dialyzer 2 to be identified. These identification means α, β are each comprised of an identification code assigned to the first connector 3 and the second connector 4, and information on the identification code is read by the reading means 13 (see FIG. 11) provided in the dialysis device main body 8, thereby making it possible to identify the specific information on the circuit 1 for blood purification or the dialyzer 2.

It is to be noted that when the first connector 3 includes a projecting portion like the retained portion 3a, the identification means α is preferably formed on the opposite side (smooth side) to the side of the retained portion 3a of the first connector 3. Similarly, when the second connector 4 includes a projecting portion like the retaining pawl 4a, the identification means β is preferably formed on the opposite side (smooth side) to the side of the retaining pawl 4a of the second connector 4. In this manner, the identification means α, β are formed on a smooth side not provided with the retained portion 3a or the retaining pawl 4a, thereby making it possible to read information by the reading means smoothly.

The identification means α, β according to the present embodiment are each comprised of a bar code (including a two-dimensional bar code called "QR Code (registered trademark)") with encoded information in a predetermined format, and information is optically readable by the reading means 13 comprised of a bar code reader. It is to be noted that the identification means α, β are not limited to a bar code or the like, and may be an object which holds information magnetically or in which a projection or the like for identification is formed (in this case, identifiable by the position or the size of a projection).

In particular, the identification means α, β according to the present embodiment allow specific information to be identified, the specific information including operating conditions of the circuit 1 for blood purification or the dialyzer 2 (the circuit 1 for blood purification or the dialyzer 2 connected to the first connector 3 or the second connector 4) at the time of blood purification treatment or preparation (such as priming) for the treatment. More specifically, the operating conditions as the specific information of the identification means α, β include a parameter indicating a restriction or an acceptable range related to blood purification treatment or preparation for the treatment, and for instance, the following may be included.

That is, the operating conditions, which are related to blood purification treatment and included in the specific information, include feasible treatment modes (such as CHD, CHF, CHDF, PE), the maximum treatment time, the upper limit and lower limit of weight of a suitable patient, the upper limit and lower limit of operational range of blood flow rate, the upper limit and lower limit of operational range of dialysate flow rate, the upper limit and lower limit of operational range of substitution fluid flow rate, the upper limit and lower limit of blood pressure for monitoring alert, the upper limit and lower limit of dialysate pressure for monitoring alert, the upper limit and lower limit of substitution fluid pressure for monitoring alert, the upper limit and lower limit of filter differential pressure for monitoring alert, the upper limit and lower limit of TMP for monitoring alert, the upper limit and lower limit of operational range of blood removal flow rate, and the upper limit and lower limit of operational range of returning blood flow rate. Also, the operating conditions related to preparation (priming) for blood purification treatment include a priming (liquid filling) flow rate, a priming time, a priming method (an operational specification of a pump or a clamp), a test method after priming, and a test passing range after priming.

Also, in addition to the above-mentioned operating conditions, the specific information of the identification means α, β according to the present embodiment includes additional information such as an expiration date of the circuit 1 for blood purification or the dialyzer 2. In addition to the expiration date, the additional information includes, for instance, the name, model number, manufacturer, manufacturer's serial number, membrane area, priming volume (volume of liquid filling), material-element, directions for use, and a sterilization method (of the circuit 1 for blood purification or the dialyzer 2 connected to the first connector 3 or the second connector 4).

Figure 11:
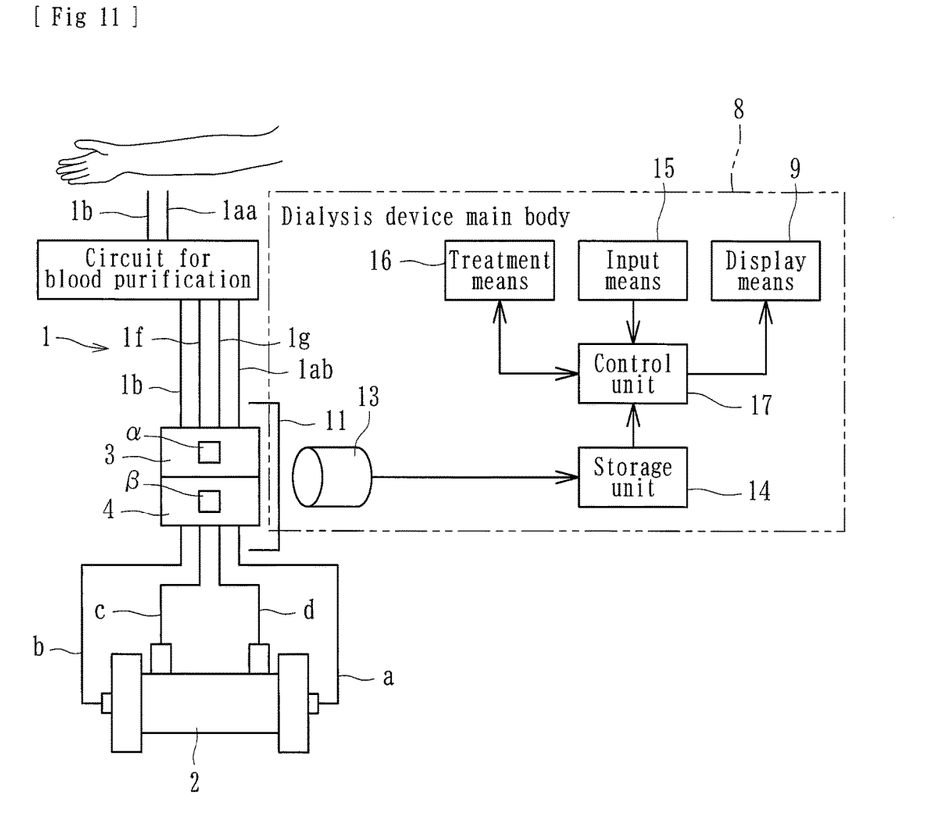
FIG. 11 is a block diagram illustrating the entire structure of the blood purification apparatus.

As illustrated in FIG. 11, the dialysis device main body 8 is provided with various treatment means 16 (an actuator such as a blood pump and sensors) for performing blood purification treatment by the blood circuits (the arterial blood circuit 1a and the venous blood circuit 1b) and the dialyzer 2 (blood purifier). In addition to the above-mentioned reading means 13, the dialysis device main body 8 includes a display means 9, a storage unit 14, an input means 15, and a control unit 17. It is to be noted that the dialysis device main body 8 includes a holding unit 10 (see FIG. 3) for holding the dialyzer 2 in a predetermined posture.

The display means 9 displays a setting value, a patient, states of devices in blood purification treatment. In the present embodiment, the display means 9 is comprised of a touch panel and can display information on the identification code read by the reading means 13. The input means 15 is provided for inputting settings for performing blood purification treatment or preparation for the treatment. In the present embodiment, the input means 15 is comprised of a touch panel used also for the display means 9. It is to be noted that the display means 9 and the input means 15 may be separately provided.

Figure 12:
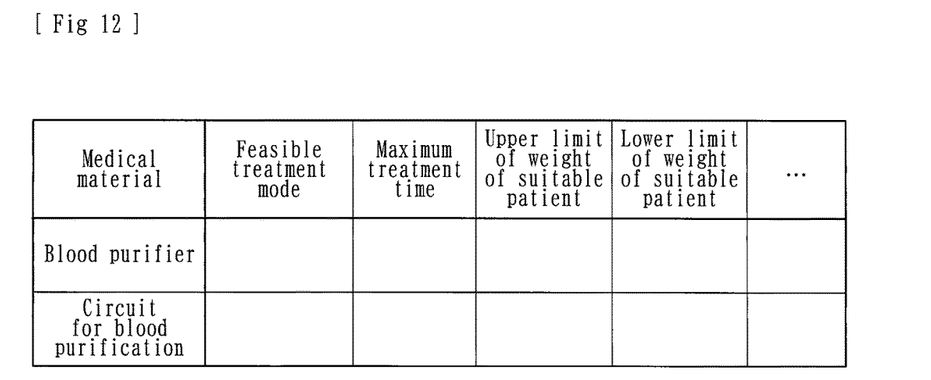
FIG. 12 is a table for storing specific information by the storage unit in the blood purification apparatus.

The storage unit 14 is comprised of a storage or the like provided in the dialysis device main body 8, and stores specific information read by the reading means 13. Specifically, the information (the operating conditions, the specification, or the additional information as the specific information) read by the reading means 13 is configured to be inputted to a table of the storage unit 14 as illustrated in FIG. 12 and stored. It is to be noted that the method of storing information by the storage unit 14 is not limited to the above-mentioned method of using a table and may be any method.

The control unit 17 is comprised of a microcomputer or the like provided in the dialysis device main body 8, and performs blood purification treatment or preparation for the treatment based on the operating conditions in the specific information read by the reading means 13. That is, after the specific information is read by the reading means 13, the control unit 17 controls the treatment means 16 to perform blood purification treatment or preparation for the treatment based on the operating conditions in the specific information stored in the storage unit 14. In addition, the control unit 17 is configured to be capable of restricting the conditions at the time of blood purification treatment based on the information identified by the identification means α, β.

On the other hand, the dialysis device main body 8 includes a holding means 11 (see FIGS. 1 to 3) that allows the first connector 3 and the second connector 4 to be held only in a state where the first connector 3 and the second connector 4 are connected, and the identification means α, β are read by the reading means 13 and identifiable in a state where the first connector 3 and the second connector 4 are held. That is, the holding means 11 is configured to be capable of holding the first connector 3 and the second connector 4 in a state where the first connector 3 and the second connector 4 are connected, and to be incapable of holding (not to hold) the first connector 3 and the second connector 4 in an unconnected state, and thus at the time of reading the identification means α, β by the reading means 13, it is always the case that the first connector 3 and the second connector 4 are connected.

However, a detection means may be provided that can detect a connection state of the first connector 3 and the second connector 4, and the dialysis device main body 8 allows liquid delivery (that is, drive of the peristaltic pumps P1 to P4) to be made by the circuit 1 for blood purification under the precondition of detection by the detection means that the first connector 3 and the second connector 4 are connected. In this manner, when a detection means is provided that can detect a connection state of the first connector 3 and the second connector 4, work or an operation according to the connection state can be performed, and when liquid delivery is made by the circuit 1 for blood purification under the precondition of detection by the detection means that the first connector 3 and the second connector 4 are connected, liquid delivery to the dialyzer 2 can be avoided in a state where the first connector 3 and the second connector 4 are not connected.

Figure 13:
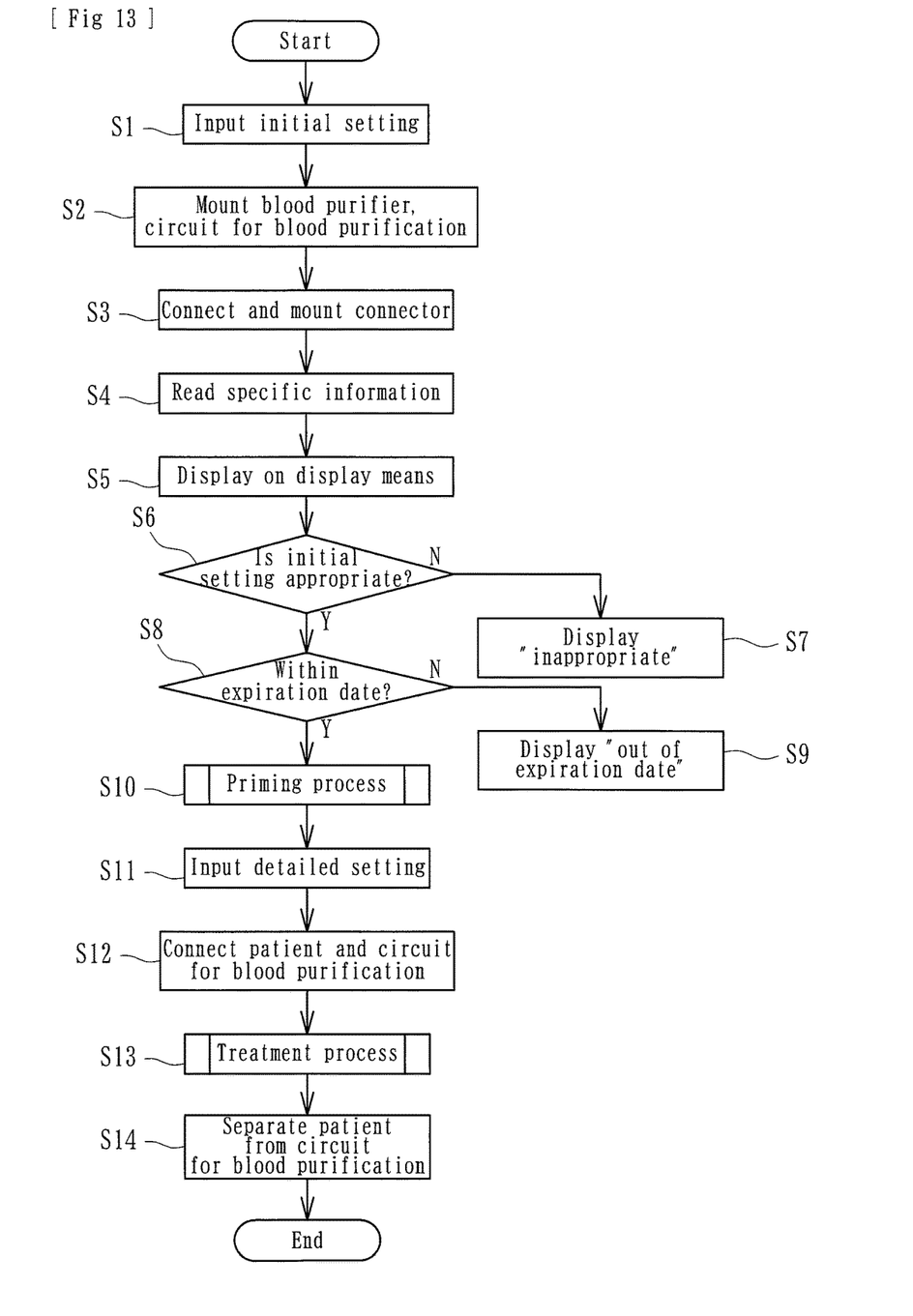
FIG. 13 is a flow chart illustrating details of control in the blood purification apparatus.

Next, details of control of the dialysis apparatus (blood purification apparatus) according to the present embodiment will be described based on the flow chart of FIG. 13.

First, in S1, a medical professional inputs initial setting by the input means 15, then mounts the dialyzer 2 and the circuit 1 for blood purification on the dialysis device main body 8 (S2), and connects the first connector 3 and the second connector 4 and causes the holding means 11 to hold the first connector 3 and the second connector 4 (S3). It is to be noted that the initial setting inputted by the input means 15 is transmitted to the control unit 17.

The specific information of the identification means α, β of the first connector 3 and the second connector 4 held by the holding means 11 is read by the reading means 13 (S4), and the read information (such as the specific information including the operating conditions or additional information) is displayed by the display means 9 (S5). It is to be noted that out of the information read by the reading means 13, particularly the specific information including the operating conditions is transmitted to the storage unit 14 and is stored, for instance in a table or the like of the storage unit 14.

Subsequently, it is determined whether or not the initial setting inputted in S1 is appropriate in consideration of the operating conditions stored in the storage unit 14 (S6). When it is determined that the initial setting is not appropriate (in other words, the initial setting is not in line with the operating conditions in the specific information), the flow proceeds to S7, and "inappropriate" is displayed, for instance, by the display means 9. When it is determined that the initial setting is appropriate (in other words, the initial setting is in line with the operating conditions in the specific information), the flow proceeds to S8.

In S8, it is determined whether or not the circuit 1 for blood purification or the dialyzer 2 is within the expiration date in consideration of the expiration date out of the information read as the additional information by the reading means 13. When it is determined that the circuit 1 for blood purification or the dialyzer 2 is out of the expiration date (in other words, the expiration date is exceeded), the flow proceeds to S9, and "out of the expiration date" is displayed, for instance, by the display means 9. When it is determined that the circuit 1 for blood purification or the dialyzer 2 is within the expiration date (in other words, the expiration date is not exceeded), the flow proceeds to S10.

In S10, priming, which is a preparation process for blood purification treatment, is performed based on the operating conditions stored in the storage unit 14. When the priming is completed, in S11, detailed setting (setting of treatment conditions related to blood purification treatment) is made by a medical professional using the input means 15, and subsequently, a puncture needle attached to the arterial blood circuit 1a and the venous blood circuit 1b is inserted in a patient to connect the patient and the circuit 1 for blood purification (S12).

Subsequently, blood purification treatment is performed based on the operating conditions stored in the storage unit 14 (S13). In S13, the control unit 17 controls the treatment means 16 based on the operating conditions stored in the storage unit 14, and appropriate blood purification treatment (dialysis treatment) is thereby performed in accordance with the operating conditions. When the blood purification treatment (including a returning blood process) is completed, the puncture needle is removed from the patient to separate the patient from the circuit 1 for blood purification (S14). Thus, a series of control is completed.

According to the above-described embodiment, the blood purification apparatus includes: the identification means α, β that allow specific information to be identified, the specific information including the operating conditions of the circuit 1 for blood purification or the dialyzer 2 (blood purifier) at the time of blood purification treatment or preparation for the treatment; the reading means 13 by which the specific information of the identification means α, β is readable; and the control unit 17 that performs blood purification treatment or preparation for the treatment based on the operating conditions in the specific information read by the reading means 13. Thus, setting work at the time of blood purification treatment or preparation for the treatment can be easily and smoothly performed.

Also, the dialysis device main body 8 includes the storage unit 14 that stores the specific information which is read by the reading means 13, and the dialysis device main body 8 causes the control unit 17 to perform blood purification treatment or preparation for the treatment based on the operating conditions in the specific information stored in the storage unit 14. Thus, blood purification treatment or preparation for the treatment can be performed more reliably. In particular, the operating conditions as the specific information in the identification means α, β include a parameter indicating a restriction or an acceptable range related to blood purification treatment or preparation for the treatment. Thus, the parameter indicating the restriction or acceptable range for the circuit 1 for blood purification or the dialyzer 2 (blood purifier) does not need to be pre-stored in the dialysis device main body 8.

Furthermore, in addition to the operating conditions, the specific information of the identification means includes additional information such as an expiration date of the circuit 1 for blood purification or the dialyzer 2 (blood purifier). Thus, blood purification treatment or preparation for the treatment can be performed by the control unit 17 based on the additional information. Also, the control unit 17 of the dialysis device main body 8 allows a treatment condition to be restricted based on the information identified by the identification means α, β. Thus, the safety of blood purification treatment can be further improved.

Furthermore, the dialyzer 2 (blood purifier) has a plurality of ports (connecting portions) connectable to the circuit 1 for blood purification, respective connection flow paths (a to d) are extended from the ports of the dialyzer 2, the dialyzer 2 and the circuit 1 for blood purification are configured to be connectable via the connection flow paths (a to d), and the blood purification apparatus comprises the first connector 3 formed by bundling the leading ends of the circuit 1 for blood purification, and the second connector 4 formed by bundling the leading ends of the connection flow paths (a to d), and connection of the first connector 3 and the second connector 4 allows the circuit 1 for blood purification corresponding to the ports of the dialyzer 2 to communicate with each other, and the identification means α, β are formed in the first connector 3 or the second connector 4. Thus, work of connection between the circuit 1 for blood purification and the dialyzer 2 can be easily performed, and setting work at the time of blood purification treatment or preparation for the treatment can be easily and smoothly performed.

Also, the dialysis device main body 8 according to the present embodiment includes the holding means 11 that allows the first connector 3 and the second connector 4 to be held only in a state where the first connector 3 and the second connector 4 are connected, and the identification means α, β allow to be identified in a state where the first connector 3 and the second connector 4 are held. Thus, at the time of identification of the identification means α, β, it is always the case that the first connector 3 and the second connector 4 are in a connected state, and failure of connection between the first connector 3 and the second connector 4 can be reliably prevented. Also, the dialysis device main body 8 allows a treatment condition to be restricted based on the information identified by the identification means. Thus, the safety of blood purification treatment can be further improved.

In addition, the first connector 3 formed by bundling the leading ends of the circuit 1 for blood purification, and the second connector 4 formed by bundling the leading ends of the connection flow paths (a to d) are provided, and connection of the first connector 3 and the second connector 4 allows the circuit 1 for blood purification corresponding to the connecting portions of the dialyzer 2 (blood purifier) to communicate with each other. Thus, work of connection between the circuit 1 for blood purification and the dialyzer 2 (blood purifier) can be easily performed, and the manufacturing cost and the cost for maintenance can be reduced.

Also, in the present embodiment, the leading ends of the dialysate inlet tubes ($1c$, $1d$, $1e$, $1f$) and the dialysate outlet tubes ($1g$, $1h$), and the leading ends of the blood circuits (the arterial blood circuit $1a$ and the venous blood circuit $1b$) are bundled together and connected to the second connector 4. Thus, connection of the first connector 3 and the second connector 4 allows the blood circuits, the dialysate inlet tubes and the dialysate outlet tubes corresponding to the connecting portions of the dialyzer 2 (blood purifier) to communicate with each other.

In particular, in a state where the first connector 3 and the second connector 4 are connected, the leading end of the circuit 1 for blood purification and the leading ends of the connection flow paths (a to d) can be sealed. Thus, at the time of liquid delivery to the dialyzer 2 (blood purifier), leakage of liquid (such as priming liquid, blood, or dialysate) can be prevented, and sealing work can be performed at the same time with the connection work. Incorrect connection at the time of connection work can be avoided by forming a mark, which allows visual identification of proper type or direction of connection, in the first connector 3 and the second connector 4.

Furthermore, the first connector 3 and the second connector 4 according to the present embodiment have the shapes (the depressed shape $3b$ and the projecting shape $4b$) that allow connection only with proper type or direction of connection. Thus, incorrect connection at the time of connection work can be reliably prevented. Also, in the first connector 3 and the second connector 4 according to the present embodiment, the identification means α, β are formed, which allow the specific information on the circuit 1 for blood purification or the dialyzer 2 to be identified. Thus, blood purification treatment according to the specific information can be performed reliably and smoothly. It is to be noted that it is sufficient that the identification means α, β be formed in at least one of the first connector 3 and the second connector 4.

Furthermore, the identification means α, β according to the present embodiment are each comprised of an identification code assigned to the first connector 3 and the second connector 4, and information on the identification code is read by the reading means 13 provided in the dialysis device main body 8 (device main body), thereby making it possible to identify the specific information on the circuit 1 for blood purification or the dialyzer 2. Thus, more specific information can be assigned. Also, the dialysis device main body 8 includes the display means 9 that can display the information on the identification code read by the reading means 13. Thus, it is possible for a medical professional to visually identify the specific information of the circuit 1 for blood purification or the dialyzer 2 (blood purifier).

Although the present embodiment has been described above, the present invention is not limited to this, and instead of the dialyzer 2, for instance, other blood purifiers (such as a hemofilter, a blood plasma separator, a blood adsorber) may be used. Alternatively, instead of the circuit 1 for blood purification, flow paths (the arterial blood circuit and the venous blood circuit) having no dialysate inlet tube and dialysate outlet tube may be used. In other words, as long as the circuit for blood purification has the arterial blood circuit 1a and the venous blood circuit 1b that constitute a blood circuit for extracorporeally circulating at least the blood of a patient, the circuit for blood purification may have no dialysate inlet tube and dialysate outlet tube or may have another flow path such as a substitution line.

Also, in the present embodiment, respective connection flow paths (a to d) are extended from the connecting portions with the circuit 1 for blood purification in the dialyzer 2, the blood purification apparatus comprises the first connector 3 formed by bundling the leading ends of the circuit 1 for blood purification, and the second connector 4 formed by bundling the leading ends of the connection flow paths (a to d), and connection of the first connector 3 and the second connector 4 allows the circuit 1 for blood purification corresponding to the connecting portions of the dialyzer 2 to communicate with each other. However, the present invention is applicable to a blood purification apparatus having no first connector 3, second connector 4, and connection flow paths (a to d). It is to be noted that applicable blood purification treatment is not limited to dialysis treatment and may be another treatment which extracorporeally circulates the blood of a patient to purify the blood.

The blood purification apparatus may have another additional function as long as the blood purification apparatus includes an identification means that allows specific information to be identified, the specific information including an operating condition of the circuit for blood purification or the blood purifier at the time of blood purification treatment or preparation for the treatment, a reading means by which the specific information of the identification means is readable, and a control unit that performs blood purification treatment or preparation for the treatment based on the operating condition in the specific information read by the reading means.

REFERENCE SIGNS LIST

1 Circuit for blood purification
1a Arterial blood circuit
1b Venous blood circuit
2 Dialyzer (blood purifier)
3 First connector
4 Second connector
5 Warming bag
6 Weight scale
7 Weight scale
8 Dialysis device main body (device main body)
9 Display means
10 Holding unit
11 Holding means
12 Cover
13 Reading means
14 Storage unit
15 Input means
16 Treatment means
17 Control unit
α, β Identification means

The invention claimed is:

1. A blood purification apparatus comprising:
a circuit for blood purification having an arterial blood circuit and a venous blood circuit that constitute a blood circuit for extracorporeally circulating at least blood of a patient;
a blood purifier for purifying the blood extracorporeally circulated by the blood circuit; and
a device main body provided with various treatment means for performing blood purification treatment in the blood circuit and the blood purifier,
wherein the blood purification apparatus includes an identification means that allows specific information to be identified, the specific information including an operating condition of the circuit for blood purification or the blood purifier at the time of blood purification treatment or preparation for the treatment, a reading means by which the specific information of the identification means is readable, and a control unit that performs blood purification treatment or preparation for the treatment based on the operating condition in the specific information read by the reading means; and
wherein the blood purifier has a plurality of connecting portions connectable to the circuit for blood purification, respective connection flow paths are extended from the connecting portions of the blood purifier, and the blood purifier and the circuit for blood purification are configured to be connectable via the connection flow paths, the blood purification apparatus comprises a first connector formed by bundling leading ends of the circuit for blood purification, and a second connector formed by bundling leading ends of the connection flow paths, and connection of the first connector and the second connector allows the circuit for blood purification corresponding to the connecting portions of the blood purifier to communicate with each other, and the identification means is formed in the first connector or the second connector.

2. The blood purification apparatus according to claim 1, wherein the device main body includes a storage unit that stores the specific information which is read by the reading means, and device main body causes the control unit to perform blood purification treatment or preparation for the treatment based on the operating condition in the specific information stored in the storage unit.

3. The blood purification apparatus according to claim 2, wherein the operating condition as the specific information in the identification means includes a parameter indicating a restriction or an acceptable range related to blood purification treatment or preparation for the treatment.

4. The blood purification apparatus according to claim 3, wherein in addition to the operating condition, the specific information of the identification means includes additional information such as an expiration date of the circuit for blood purification or the blood purifier.

5. The blood purification apparatus according to claim 2, wherein in addition to the operating condition, the specific information of the identification means includes additional information such as an expiration date of the circuit for blood purification or the blood purifier.

6. The blood purification apparatus according to claim 2, wherein the control unit of the device main body allows a treatment condition to be restricted based on information identified by the identification means.

7. The blood purification apparatus according to claim 2, wherein the device main body includes a holding means that allows the first connector and the second connector to be held only in a state where the first connector and the second connector are connected, and the identification means allows to be identified in a state where the first connector and the second connector are held.

8. The blood purification apparatus according to claim 1, wherein in addition to the operating condition, the specific information of the identification means includes additional information such as an expiration date of the circuit for blood purification or the blood purifier.

9. The blood purification apparatus according to claim 8, wherein the control unit of the device main body allows a treatment condition to be restricted based on information identified by the identification means.

10. The blood purification apparatus according to claim 1, wherein the device main body includes a holding means that allows the first connector and the second connector to be held only in a state where the first connector and the second connector are connected, and the identification means allows to be identified in a state where the first connector and the second connector are held.

11. A blood purification apparatus comprising:
a circuit for blood purification having an arterial blood circuit and a venous blood circuit that constitute a blood circuit for extracorporeally circulating at least blood of a patient;
a blood purifier for purifying the blood extracorporeally circulated by the blood circuit; and
a device main body provided with various treatment means for performing blood purification treatment in the blood circuit and the blood purifier,
wherein the blood purification apparatus includes an identification means that allows specific information to be identified, the specific information including an operating condition of the circuit for blood purification or the blood purifier at the time of blood purification treatment or preparation for the treatment, a reading means by which the specific information of the identification means is readable, and a control unit that performs blood purification treatment or preparation for the treatment based on the operating condition in the specific information read by the reading means, the control unit allowing a treatment condition to be restricted based on information identified by the identification means; and
wherein the operating condition as the specific information in the identification means includes a parameter indicating a restriction or an acceptable range related to blood purification treatment or preparation for the treatment.

12. The blood purification apparatus according to claim 11, wherein the blood purifier has a plurality of connecting portions connectable to the circuit for blood purification, respective connection flow paths are extended from the connecting portions of the blood purifier, and the blood purifier and the circuit for blood purification are configured to be connectable via the connection flow paths, the blood purification apparatus comprises a first connector formed by bundling leading ends of the circuit for blood purification, and a second connector formed by bundling leading ends of the connection flow paths, and connection of the first connector and the second connector allows the circuit for blood purification corresponding to the connecting portions of the blood purifier to communicate with each other, and the identification means is formed in the first connector or the second connector.

* * * * *